(12) United States Patent
Friedman et al.

(10) Patent No.: US 7,943,302 B2
(45) Date of Patent: May 17, 2011

(54) C20ORF23 AS MODIFIER OF THE IGFR PATHWAY AND METHODS OF USE

(75) Inventors: Lori Friedman, San Carlos, CA (US); Helen Francis-Lang, San Francisco, CA (US); Annette L. Parks, Newton, MA (US); Kenneth James Shaw, Brisbane, CA (US); Lynn Margaret Bjerke, Sutton (GB); Timothy S. Heuer, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 423 days.

(21) Appl. No.: 10/592,171

(22) PCT Filed: Mar. 10, 2005

(86) PCT No.: PCT/US2005/008127
§ 371 (c)(1),
(2), (4) Date: Apr. 1, 2009

(87) PCT Pub. No.: WO2005/090977
PCT Pub. Date: Sep. 29, 2005

(65) Prior Publication Data
US 2009/0202563 A1 Aug. 13, 2009

Related U.S. Application Data

(60) Provisional application No. 60/552,634, filed on Mar. 12, 2004.

(51) Int. Cl.
*C12Q 1/68* (2006.01)
*G01N 33/53* (2006.01)
*C07H 21/04* (2006.01)
*C07K 14/435* (2006.01)

(52) U.S. Cl. ............ 435/6; 435/7.1; 536/23.5; 530/350
(58) Field of Classification Search ........................ None
See application file for complete search history.

(56) References Cited

U.S. PATENT DOCUMENTS
2006/0019256 A1* 1/2006 Clarke et al. .................... 435/6

FOREIGN PATENT DOCUMENTS
WO WO 2004/065545 A2 8/2004

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells, J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Wang et al. Rapid analysis of gene expression (RAGE) facilitates universal expression filing. Nucleic Acid Res 27(23): 4609-4618, 1999.*
Kaufman et al. Transgenic analysis of a 100-kb human beta blobin cluster-containing DNA fragment propogated as a bacterial artifical chromosome. Blood 94(9): 3178-3184, 1999.*
Hoepfner Sebastian et al.: "Modulation of receptor recycling and degradation by the endosomal kinesin KIF16B," Cell, May 6, 2005, vol. 121, No. 3, pp. 437-450.
Shmueli O. et al.: "GeneNote: whole genome expression profiles in normal human tissues," Comptes Rendus—Biologies, Elsevier, Pairs, France, vol. 326, No. 10-11, Oct. 2003, pp. 1067-1072.
O'Connor R.: "Regulation of IGF-I Receptor Signaling in Tumor Cells," Hormone and Metabolic Research, Thieme-Stratton, Stuttgart, DE, vol. 35, No. 11/12, Nov. 2003, pp. 771-777.
O'Connor R. et al.: "Regulation of survival signals from the insulin-like growth factor-I receptor," Biochemical Society Transactions, Colchester, Essex, GB, vol. 28, No. 2, Feb. 2000, pp. 47-51.
Polonsky, K.S. The beta-cell in Diabetes: from molecular genetics to clinical research. Diabetes, Jun. 1995, vol. 44, No. 6, pp. 705-717, see entire document.
Butler M.G. Imprinting disorders: non-Mendelian mechanisms affecting growth. Journal of Pediatric Endocrinology & Metabolism, 2002, vol. 15, Suppl. 5, pp. 1279-1288, Abstract only. See abstract.

* cited by examiner

*Primary Examiner* — Bridget E Bunner
(74) *Attorney, Agent, or Firm* — McDonnell Boehnen Hulbert & Berghoff LLP

(57) ABSTRACT

Human C20ORF23 genes are identified as modulators of the IGFR pathway, and thus are therapeutic targets for disorders associated with defective IGFR function. Methods for identifying modulators of IGFR, comprising screening for agents that modulate the activity of C20ORF23 are provided.

7 Claims, No Drawings

C20ORF23 AS MODIFIER OF THE IGFR PATHWAY AND METHODS OF USE

REFERENCE TO RELATED APPLICATIONS

This application claims priority to U.S. provisional patent application 60/552,634 filed Mar. 12, 2004. The contents of the prior application are hereby incorporated in their entirety.

BACKGROUND OF THE INVENTION

Somatic mutations in the PTEN (Phosphatase and Tensin homolog deleted on chromosome 10) gene are known to cause tumors in a variety of human tissues. In addition, germline mutations in PTEN are the cause of human diseases (Cowden disease and Bannayan-Zonana syndrome) associated with increased risk of breast and thyroid cancer (Nelen M R et al. (1997) Hum Mol Genet, 8:1383-1387; Liaw D et al. (1997) Nat Genet, 1:64-67; Marsh D J et al. (1998) Hum Mol Genet, 3:507-515). PTEN is thought to act as a tumor suppressor by regulating several signaling pathways through the second messenger phosphatidylinositol 3,4,5 triphosphate (PIP3). PTEN dephosphorylates the D3 position of PIP3 and down-regulates signaling events dependent on PIP3 levels (Maehama T and Dixon J E (1998) J Biol Chem, 22, 13375-8). In particular, pro-survival pathways downstream of the insulin-like growth factor (IGF) pathway are regulated by PTEN activity. Stimulation of the IGF pathway, or loss of PTEN function, elevates PIP3 levels and activates pro-survival pathways associated with tumorigenesis (Stambolic V et al. (1998) Cell, 95:29-39). Consistent with this model, elevated levels of insulin-like growth factors I and II correlate with increased risk of cancer (Yu H et al (1999) J Natl Cancer Inst 91:151-156) and poor prognosis (Takanami I et al, 1996, J Surg Oncol 61(3):205-8). In addition, increased levels or activity of positive effectors of the IGF pathway, such as Akt and PI(3) kinase, have been implicated in several types of human cancer (Nicholson KM and Anderson NG (2002) Cellular Signalling, 14:381-395).

In *Drosophila melanogaster*, as in vertebrates, the Insulin Growth Factor Receptor (IGFR) pathway includes the positive effectors PI(3) kinase, Akt, and PDK and the inhibitor, PTEN. These proteins have been implicated in multiple processes, including the regulation of cell growth and size as well as cell division and survival (Oldham S and Hafen E. (2003) Trends Cell Biol. 13:79-85; Garafolo R S. (2002) Trends Endocr. Metab. 13:156-162; Backman S A et al. (2002) Curr. Op. Neurobio. 12:1-7; Tapon N et al. (2001) Curr Op. Cell Biol. 13:731-737). Activation of the pathway in Drosophila can result in increases in cell size, cell number and organ size (Oldham S et al. (2002) Dev. 129:4103-4109; Prober D A and Edgar B A. (2002) Genes & Dev. 16:2286-2299; Potter C J et al. (2001) Cell 105:357-368; Verdu J et al. (1999) Cell Biol. 1:500-506).

Sorting nexins are a diverse group of cellular trafficking proteins that are unified by the presence of a phospholipid-binding motif—the PX domain. The ability of these proteins to bind specific phospholipids, as well as their propensity to form protein-protein complexes, points to a role for these proteins in membrane trafficking and protein sorting. Chromosome 20 open reading frame 23 (C20ORF23) is a kinesin protein belonging to the sorting nexin family of proteins.

The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as IGFR, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the IGFR pathway in Drosophila, and identified their human orthologs, hereinafter referred to as C20ORF23. The invention provides methods for utilizing these IGFR modifier genes and polypeptides to identify C20ORF23-modulating agents that are candidate therapeutic agents that can be used in the treatment of disorders associated with defective or impaired IGFR function and/or C20ORF23 function. Preferred C20ORF23-modulating agents specifically bind to C20ORF23 polypeptides and restore IGFR function. Other preferred C20ORF23-modulating agents are nucleic acid modulators such as antisense oligomers and RNAi that repress C20ORF23 gene expression or product activity by, for example, binding to and inhibiting the respective nucleic acid (i.e. DNA or mRNA).

C20ORF23 modulating agents may be evaluated by any convenient in vitro or in vivo assay for molecular interaction with a C20ORF23 polypeptide or nucleic acid. In one embodiment, candidate C20ORF23 modulating agents are tested with an assay system comprising a C20ORF23 polypeptide or nucleic acid. Agents that produce a change in the activity of the assay system relative to controls are identified as candidate IGF modulating agents. The assay system may be cell-based or cell-free. C20ORF23-modulating agents include C20ORF23 related proteins (e.g. dominant negative mutants, and biotherapeutics); C20ORF23-specific antibodies; C20ORF23-specific antisense oligomers and other nucleic acid modulators; and chemical agents that specifically bind to or interact with C20ORF23 or compete with C20ORF23 binding partner (e.g. by binding to a C20ORF23 binding partner). In one specific embodiment, a small molecule modulator is identified using an ATPase assay. In specific embodiments, the screening assay system is selected from a binding assay, an apoptosis assay, a cell proliferation assay, an angiogenesis assay, and a bypoxic induction assay.

In another embodiment, candidate IGFR pathway modulating agents are further tested using a second assay system that detects changes in the IGFR pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the IGFR pathway, such as an angiogenic, apoptotic, or cell proliferation disorder (e.g. cancer).

The invention further provides methods for modulating the C20ORF23 function and/or the IGFR pathway in a mammalian cell by contacting the mammalian cell with an agent that specifically binds a C20ORF23 polypeptide or nucleic acid. The agent may be a small molecule modulator, a nucleic acid modulator, or an antibody and may be administered to a mammalian animal predetermined to have a pathology associated with the IGFR pathway.

DETAILED DESCRIPTION OF THE INVENTION

A dominant loss of function screen was carried out in Drosophila to identify genes that interact with or modulate the IGFR signaling pathway. Modifiers of the IGFR pathway and their orthologs were identified. The KLP98A gene was identified as a modifier of the IGFR pathway. Accordingly, vertebrate orthologs of these modifiers, and preferably the human orthologs, C20ORF23 genes (i.e., nucleic acids and polypeptides) are attractive drug targets for the treatment of pathologies associated with a defective IGFR signaling pathway, such as cancer.

In vitro and in vivo methods of assessing C20ORF23 function are provided herein. Modulation of the C20ORF23 or their respective binding partners is useful for understanding the association of the IGFR pathway and its members in normal and disease conditions and for developing diagnostics and therapeutic modalities for IGFR related pathologies. C20ORF23-modulating agents that act by inhibiting or enhancing C20ORF23 expression, directly or indirectly, for example, by affecting a C20ORF23 function such as enzymatic (e.g., catalytic) or binding activity, can be identified using methods provided herein. C20ORF23 modulating agents are useful in diagnosis, therapy and pharmaceutical development.

Nucleic Acids and Polypeptides of the Invention

Sequences related to C20ORF23 nucleic acids and polypeptides that can be used in the invention are disclosed in Genbank (referenced by Genbank identifier (GI) number) as GI#s 31077078 (SEQ ID NO:1), 28395018 (SEQ ID NO:2), 34366729 (SEQ ID NO:3), 27529916 (SEQ ID NO:4), and 23271548 (SEQ ID NO:5) for nucleic acid, and GI# 28395029 (SEQ ID NO:6) for polypeptide sequences.

The term "C20ORF23 polypeptide" refers to a full-length C20ORF23 protein or a functionally active fragment or derivative thereof. A "functionally active" C20ORF23 fragment or derivative exhibits one or more functional activities associated with a full-length, wild-type C20ORF23 protein, such as antigenic or immunogenic activity, enzymatic activity, ability to bind natural cellular substrates, etc. The functional activity of C20ORF23 proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active C20ORF23 polypeptide is a C20ORF23 derivative capable of rescuing defective endogenous C20ORF23 activity, such as in cell based or animal assays; the rescuing derivative may be from the same or a different species. For purposes herein, functionally active fragments also include those fragments that comprise one or more structural domains of a C20ORF23, such as a binding domain. Protein domains can be identified using the PFAM program (Bateman A., et al., Nucleic Acids Res, 1999, 27:260-2). For example, the kinesin motor domain (PFAM 00225) of C20ORF23 from GI# 28395029 (SEQ ID NO:6) is located at approximately amino acid residues 9 to 359. Methods for obtaining C20ORF23 polypeptides are also further described below. In some embodiments, preferred fragments are functionally active, domain-containing fragments comprising at least 25 contiguous amino acids, preferably at least 50, more preferably 75, and most preferably at least 100 contiguous amino acids of a C20ORF23. In further preferred embodiments, the fragment comprises the entire functionally active domain.

The term "C20ORF23 nucleic acid" refers to a DNA or RNA molecule that encodes a C20ORF23 polypeptide. Preferably, the C20ORF23 polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human C20ORF23. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows specification, a single gene in one species, such as Drosophila, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program VU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195197; Nicholas et al., 1998, "A Tutorial on Searching Sequence Databases and Sequence Scoring Methods" and references cited therein; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of a C20ORF23. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of a C20ORF23 under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCI (pH7.5), 5 mM EDTA, 0.1% PVP, 0.1% FICOLL®, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-expression of C20ORF23 Nucleic Acids and Polypeptides C20ORF23 nucleic acids and polypeptides are useful for identifying and testing agents that modulate C20ORF23 function and for other applications related to the involvement of C20ORF23 in the IGFR pathway. C20ORF23 nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a C20ORF23 protein for assays used to assess C20ORF23 function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant C20ORF23 is expressed in a cell line known to have defective IGFR function The recombinant cells are used in cell-based screening assay systems of the invention, as described further below.

The nucleotide sequence encoding a C20ORF23 polypeptide can be inserted into any appropriate expression vector. The necessary transcriptional and translational signals, including promoter/enhancer element, can derive from the native C20ORF23 gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the C20ORF23 gene product, the expression vector can comprise a promoter operably linked to a C20ORF23 gene nucleic acid, one or more origins of replication, and, one or more selectable markers (e.g. thymidine kinase activity, resistance to antibiotics, etc.). Alternatively, recombinant expression vectors can be identified by assaying for the expression of the C20ORF23 gene product based on the physical or functional properties of the C20ORF23 protein in in vitro assay systems (e.g. immunoassays).

The C20ORF23 protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the C20ORF23 gene sequence is identified, the gene product can be isolated and purified using standard methods (e.g. ion exchange, affinity, and gel exclusion chromatography; centrifugation; differential solubility; electrophoresis). Alternatively, native C20ORF23 proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of C20ORF23 or other genes associated with the IGFR pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter C20ORF23 expression may be used in in vivo assays to test for activity of a candidate IGFR modulating agent, or to further assess the role of C20ORF23 in a IGFR pathway process such as apoptosis or cell proliferation. Preferably, the altered C20ORF23 expression results in a detectable phenotype, such as decreased or increased levels of cell proliferation, angiogenesis, or apoptosis compared to control animals having normal C20ORF23 expression. The genetically modified animal may additionally have altered IGFR expression (e.g. IGFR knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous C20ORF23 gene that results in a decrease of C20ORF23 function, preferably such that C20ORF23 expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse C00ORF23 gene is used to construct a homologous recombination vector suitable for altering an endogenous C20ORF23 gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270:8397-400).

In another embodiment, the transgenic animal is a "knock-in" animal having an alteration in its genome that results in altered expression (e.g., increased (including ectopic) or decreased expression) of the C20ORF23 gene, e.g., by introduction of additional copies of C20ORF23, or by operatively inserting a regulatory sequence that provides for altered expression of an endogenous copy of the C20ORF23 gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxp recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the IGFR pathway, as animal models of disease and disorders implicating defective IGFR function, and for in vivo testing of candidate therapeutic agents, such as those identified in screens described below. The candidate therapeutic agents are administered to a genetically modified animal having altered C20ORF23 function and phenotypic changes are compared with appropriate control animals such as genetically modified animals that receive placebo treatment, and/or animals with unaltered C20ORF23 expression that receive candidate therapeutic agent.

In addition to the above-described genetically modified animals having altered C20ORF23 function, animal models having defective IGFR function (and otherwise normal C20ORF23 function), can be used in the methods of the present invention. For example, a IGFR knockout mouse can be used to assess, in vivo, the activity of a candidate IGFR modulating agent identified in one of the in vitro assays described below. Preferably, the candidate IGFR modulating agent when administered to a model system with cells defective in IGFR function, produces a detectable phenotypic change in the model system indicating that the IGFR function is restored, i.e., the cells exhibit normal cell cycle progression.

Modulating Agents

The invention provides methods to identify agents that interact with and/or modulate the function of C20ORF23 and/or the IGFR pathway. Modulating agents identified by the methods are also part of the invention. Such agents are useful in a variety of diagnostic and therapeutic applications associated with the IGFR pathway, as well as in further analysis of the C20ORF23 protein and its contribution to the IGFR pathway. Accordingly, the invention also provides methods for modulating the IGFR pathway comprising the step of specifically modulating C20ORF23 activity by administering a C20ORF23-interacting or -modulating agent.

As used herein, a "C20ORF23-modulating agent" is any agent that modulates C20ORF23 function, for example, an agent that interacts with C20ORF23 to inhibit or enhance C20ORF23 activity or otherwise affect normal C20ORF23 function. C20ORF23 function can be affected at any level, including transcription, protein expression, protein localization, and cellular or extra-cellular activity. In a preferred embodiment, the C20ORF23-modulating agent specifically modulates the function of the C20ORF23. The phrases "specific modulating agent", "specifically modulates", etc., are used herein to refer to modulating agents that directly bind to the C20ORF23 polypeptide or nucleic acid, and preferably inhibit, enhance, or otherwise alter, the function of the C20ORF23. These phrases also encompass modulating agents that alter the interaction of the C20ORF23 with a binding partner, substrate, or cofactor (e.g. by binding to a binding partner of a C20ORF23, or to a protein/binding partner complex, and altering C20ORF23 function). In a further preferred embodiment, the C20ORF23-modulating agent is a modulator of the IGFR pathway (e.g. it restores and/or upregulates IGFR function) and thus is also a IGFR-modulating agent.

Preferred C20ORF23-modulating agents include small molecule compounds; C20ORF23-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the C20ORF23 protein or may be identified by screening compound libraries. Alternative appropriate modulators of this class are natural products, particularly secondary metabolites from organisms such as plants or fungi, which can also be identified by screening compound libraries for C20ORF23-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the IGFR pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific C20ORF23-interacting proteins are useful in a variety of diagnostic and therapeutic applications related to the IGFR pathway and related disorders, as well as in validation assays for other C20ORF23-modulating agents. In a preferred embodiment, C20ORF23-interacting proteins affect normal C20ORF23 function, including transcription, protein expression, protein localization, and cellular or extra-cellular activity. In another embodiment, C20ORF23-interacting proteins are useful in detecting and providing information about the function of C20ORF23 proteins, as is relevant to IGFR related disorders, such as cancer (e.g., for diagnostic means).

A C20ORF23-interacting protein may be endogenous, i.e. one that naturally interacts genetically or biochemically with a C20ORF23, such as a member of the C20ORF23 pathway that modulates C20ORF23 expression, localization, and/or activity. C20ORF23-modulators include dominant negative forms of C20ORF23-interacting proteins and of C20ORF23 proteins themselves. Yeast two-hybrid and variant screens offer preferred methods for identifying endogenous C20ORF23-interacting proteins Finley, R. L. et al. (1996) in DNA Cloning-Expression Systems: A Practical Approach, eds. Glover D. & Hames B. D (Oxford University Press, Oxford, England), pp. 169-203; Fashema SF et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An C20ORF23-interacting protein may be an exogenous protein, such as a C20ORF23-specific antibody or a T-ell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). C20ORF23 antibodies are further discussed below.

In preferred embodiments, a C20ORF23-interacting protein specifically binds a C20ORF23 protein. In alternative preferred embodiments, a C20ORF23-modulating agent binds a C20ORF23 substrate, binding partner, or cofactor.

Antibodies

In another embodiment, the protein modulator is a C20ORF23 specific antibody agonist or antagonist. The antibodies have therapeutic and diagnostic utilities, and can be used in screening assays to identify C20ORF23 modulators. The antibodies can also be used in dissecting the portions of the C20ORF23 pathway responsible for various cellular responses and in the general processing and maturation of the C20ORF23.

Antibodies that specifically bind C20ORF23 polypeptides can be generated using known methods. Preferably the antibody is specific to a mammalian ortholog of C20ORF23 polypeptide, and more preferably, to human C20ORF23. Antibodies may be polyclonal, monoclonal (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Epitopes of C20ORF23 which are particularly antigenic can be selected, for example, by routine screening of C20ORF23 polypeptides for antigenicity or by applying a theoretical method for selecting antigenic regions of a protein (Hopp and Wood (1981), Proc. Natl. Acad. Sci. U.S.A. 78:382-428; Hopp and Wood, (1983) Mol. Immunol. 20:483-89; Sutcliffe et al., (1983) Science 219:660-66) to the amino acid sequence of a C20ORF23. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of C20ORF23 or substantially purified fragments thereof. If C20ORF23 fragments are used, they preferably comprise at least 10, and more preferably, at least 20 contiguous amino acids of a C20ORF23 protein. In a particular embodiment, C20ORF23-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of C20ORF23-specific antibodies is assayed by an appropriate assay such as a solid phase enzyme-linked immunosorbant assay (ELISA) using immobilized corresponding C20ORF23 polypeptides. Other assays, such as radioimmunoassays or fluorescent assays might also be used.

Chimeric antibodies specific to C20ORF23 polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

C20ORF23-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988% supra).

The polypeptides and antibodies of the present invention may be used with or without modification. Frequently, antibodies will be labeled by joining, either covalently or noncovalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg—to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred C20ORF23-modulating agents comprise nucleic acid molecules, such as antisense oligomers or double stranded RNA (dsRNA), which generally inhibit C20ORF23 activity. Preferred nucleic acid modulators interfere with the function of the C20ORF23 nucleic acid such as DNA replication, transcription, translocation of the C20ORF23 RNA to the site of protein translation, translation of protein from the C20ORF23 RNA, splicing of the C20ORF23 RNA to yield one or more mRNA species, or catalytic activity which may be engaged in or facilitated by the C20ORF23 RNA.

In one embodiment, the antisense oligomer is an oligonucleotide that is sufficiently complementary to a C20ORF23 mRNA to bind to and prevent translation, preferably by binding to the 5' untranslated region. C20ORF23-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev. 7:187-95; U.S. Pat. No. 5,235,033; and U.S. Pat. No. 5,378,841).

Alternative preferred C20ORF23 nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a C20ORF23-specific nucleic acid modulator is used in an assay to further elucidate the role of the C20ORF23 in the IGFR pathway, and/or its relationship to other members of the pathway. In another aspect of the invention, a C20ORF23-specific antisense oligomer is used as a therapeutic agent for treatment of IGFR-related disease states.

Assay Systems

The invention provides assay systems and screening methods for identifying specific modulators of C20ORF23 activity. As used herein, an "assay system" encompasses all the components required for performing and analyzing results of an assay that detects and/or measures a particular event. In general, primary assays are used to identify or confirm a modulator's specific biochemical or molecular effect with respect to the C20ORF23 nucleic acid or protein. In general, secondary assays further assess the activity of a C20ORF23 modulating agent identified by a primary assay and may confirm that the modulating agent affects C20ORF23 in a manner relevant to the IGFR pathway. In some cases, C20ORF23 modulators will be directly tested in a secondary assay.

In a preferred embodiment, the screening method comprises contacting a suitable assay system comprising a C20ORF23 polypeptide or nucleic acid with a candidate agent under conditions whereby, but for the presence of the agent, the system provides a reference activity (e.g. ATPase activity), which is based on the particular molecular event the screening method detects. A statistically significant difference between the agent-biased activity and the reference activity indicates that the candidate agent modulates C20ORF23 activity, and hence the IGFR pathway. The C20ORF23 polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of C20ORF23 and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when C20ORF23-interacting proteins are used in screens to identify small molecule modulators, the binding specificity of the interacting protein to the C20ORF23 protein may be assayed by various known methods such as substrate processing (e.g. ability of the candidate C20ORF23-specific binding agents to function as negative effectors in C20ORF23-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit C20ORF23 specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a C20ORF23 polypeptide, a fusion protein thereof, or to cells or membranes bearing the polypeptide or fusion protein. The C20ORF23 polypeptide can be full length or a fragment thereof that retains functional C20ORF23 activity. The C20ORF23 polypeptide may be fused to another polypeptide, such as a peptide tag for detection or anchoring, or to another tag. The C20ORF23 polypeptide is preferably human C20ORF23, or is an ortholog or derivative thereof as described above. In a preferred embodiment, the screening assay detects candidate agent-based modulation of C20ORF23 interaction with a binding target, such as an endogenous or exogenous protein or other substrate that has C20ORF23—specific binding activity, and can be used to assess normal C20ORF23 gene function.

Suitable assay formats that may be adapted to screen for C20ORF23 modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate C20ORF23 and IGFR pathway modulators (e.g. U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Kinesins are motor proteins. Assays for kinesins involve their ATPase activity, such as described in Blackburn et al (Blackburn C L, et al., (1999) J Org Chem 64:5565-5570). The ATPase assay is performed using the EnzCheck ATPase kit (Molecular Probes). The assays are performed using an Ultraspec spectrophotometer (Phamacia), and the progress of the reaction are monitored by absorbance increase at 360 nm. Microtubules (1.7 mM final), kinesin (0.11 mM final), inhibitor (or DMSO blank at 5% final), and the EnzCheck components (purine nucleotide phosphorylase and MESG substrate) are premixed in the cuvette in a reaction buffer (40 mM PIPES pH 6.8, 5 mM paclitaxel, 1 mM EGTA, 5 mM MgCl2). The reaction is initiated by addition of MGATP (1 mM final).

Apoptosis assays. Apoptosis or programmed cell death is a suicide program that is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al. 1994, Nature 371, 346), by following the incorporation of fluorescein-dUTP (Yonehara et al. 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available APO-ONE™ Homogeneous Caspase-3/7 assay from Promega, cat# 67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat# 1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumulation in the cytoplasm. Nucleosomes are not present in the cytoplasmic fraction of cells that are not undergoing apoptosis. The Phospho-histone H2B assay is another apoptosis assay, based on phosphorylation of histone H2B as a result of apoptosis. Fluorescent dyes that are associated with phospho-histone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as ™ ARRAYSCAN® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses a C20ORF23, and that optionally has defective IGFR function (e.g. IGFR is over-expressed or under-expressed relative to wild-type cells). A test agent can be added to the apoptosis assay system and changes in induction of apoptosis relative to controls where no test agent is added, identify candidate IGFR modulating agents. In some embodiments of the invention, an apoptosis assay may be used as a secondary assay to test a candidate IGFR modulating agents that is initially identified using a cell-free assay system. An apoptosis assay may also be used to test whether C20ORF23 function plays a direct role in apoptosis. For example, an apoptosis assay may be performed on cells that over- or under-express C20ORF23 relative to wild type cells. Differences in apoptotic response compared to wild type cells suggests that the C20ORF23 plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CELLTITER 96® AQueous Non-Radioactive Cell Proliferation Assay (Cat.# G5421).

Cell proliferation may also be assayed by colony formation in soft agar, or clonogenic survival assay (Sambrook et al., Molecular Cloning, Cold Spring Harbor (1989)). For example, cells transformed with C20ORF23 are seeded in soft agar plates, and colonies are measured and counted after two weeks incubation.

Cell proliferation may also be assayed by measuring ATP levels as indicator of metabolically active cells. Such assays are commercially available, for example CELL TITER-GLO™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with a C20ORF23 may be stained with propidium iodide and evaluated in a flow cytometer (available from Becton Dickinson), which indicates accumulation of cells in different stages of the cell cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of PI3 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).

Accordingly, a cell proliferation or cell cycle assay system may comprise a cell that expresses a C20ORF23, and that optionally has defective IGFR function (e.g. IGFR is over-expressed or under-expressed relative to wild-type cells). A test agent can be added to the assay system and changes in cell proliferation or cell cycle relative to controls where no test agent is added, identify candidate IGFR modulating agents. In some embodiments of the invention, the cell proliferation or cell cycle assay may be used as a secondary assay to test a candidate IGFR modulating agents that is initially identified using another assay system such as a cell-free assay system. A cell proliferation assay may also be used to test whether C20ORF23 function plays a direct role in cell proliferation or cell cycle. For example, a cell proliferation or cell cycle assay may be performed on cells that over- or under-express C20ORF23 relative to wild type cells. Differences in proliferation or cell cycle compared to wild type cells suggests that the C20ORF23 plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses a C20ORF23, and that optionally has defective IGFR function (e.g. IGFR is over-expressed or under-expressed relative to wild-type cells). A test agent can be added to the angiogenesis assay system and changes in angiogenesis relative to controls where no test agent is added, identify candidate IGFR modulating agents. In some embodiments of the invention, the angiogenesis assay may be used as a secondary assay to test a candidate IGFR modulating agents that is initially identified using another assay system. An angiogenesis assay may also be used to test whether C20ORF23 function plays a direct role in cell proliferation. For example, an angiogenesis assay may be performed on cells that over- or under-express C20ORF23 relative to wild type cells. Differences in angiogenesis compared to wild type cells suggest that the C20ORF23 plays a direct role in angiogenesis. U.S. Pat. Nos. 5,976,782, 6,225,118 and 6,444,434, among others, describe various angiogenesis assays.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with C20ORF23 in hypoxic conditions (such as with 0.1% O2, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses a C20ORF23, and that optionally has defective IGFR function (e.g. IGFR is over-expressed or under-expressed relative to wild-type cells). A test agent can be added to the hypoxic induction assay system and changes in hypoxic response relative to controls where no test agent is added, identify candidate IGFR modulating agents. In some embodiments of the invention, the hypoxic induction assay may be used as a secondary assay to test a candidate IGFR modulating agents that is initially identified using another assay system. A hypoxic induction assay may also be used to test whether C20ORF23 function plays a direct role in the hypoxic response. For example, a hypoxic induction assay may be performed on cells that over- or under-express C20ORF23 relative to wild type cells. Differences in hypoxic response compared to wild type cells suggest that the C20ORF23 plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the C20ORF23 protein. Methods for testing antibody affinity and specificity are well known in the art (Harlow and Lane, 1988, 1999, supra). The enzyme-linked immunosorbant assay (ELISA) is a preferred method for detecting C20ORF23-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance C20ORF23 gene expression, preferably mRNA expression. In general, expression analysis comprises comparing C20ORF23 expression in like populations of cells (e.g., two pools of cells that endogenously or recombinantly express C20ORF23) in the presence and absence of the nucleic acid modulator. Methods for analyzing mRNA and protein expression are well known in the art. For instance, Northern blotting, slot blotting, ribonuclease protection, quantitative RT-PCR (e.g., using the TAQMAN®, PE APPLIED BIOSYSTEMS®), or microarray analysis may be used to confirm that C20ORF23 mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the C20ORF23 protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve C20ORF23 mRNA expression, may also be used to test nucleic acid modulators.

Secondary Assays

Secondary assays may be used to further assess the activity of C20ORF23-modulating agent identified by any of the above methods to confirm that the modulating agent affects C20ORF23 in a manner relevant to the IGFR pathway. As used herein, C20ORF23-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with C20ORF23.

Secondary assays generally compare like populations of cells or animals (e.g., two pools of cells or animals that endogenously or recombinantly express C20ORF23) in the presence and absence of the candidate modulator. In general, such assays test whether treatment of cells or animals with a candidate C20ORF23-modulating agent results in changes in the IGFR pathway in comparison to untreated (or mock- or placebo-treated) cells or animals. Certain assays use "sensitized genetic backgrounds", which, as used herein, describe cells or animals engineered for altered expression of genes in the IGFR or interacting pathways.

Cell-Based Assays

Cell based assays may detect endogenous IGFR pathway activity or may rely on recombinant expression of IGFR pathway components. Any of the aforementioned assays may be used in this cell-based format. Candidate modulators are typically added to the cell media but may also be injected into cells or delivered by any other efficacious means.

Animal Assays

A variety of non-human animal models of normal or defective IGFR pathway may be used to test candidate C20ORF23 modulators. Models for defective IGFR pathway typically use genetically modified animals that have been engineered to mis-express (e.g., over-express or lack expression in) genes involved in the IGFR pathway. Assays generally require systemic delivery of the candidate modulators, such as by oral administration, injection, etc.

In a preferred embodiment, PTEN pathway activity is assessed by monitoring neovascularization and angiogenesis. Animal models with defective and normal IGFR are used to test the candidate modulator's effect on C20ORF23 in MATRIGEL® assays. MATRIGEL® is an extract of basement membrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which over-express the C20ORF23. The mixture is then injected subcutaneously (SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on C20ORF23 is assessed via tumorigenicity assays. Tumor xenograft assays are known in the art (se, e.g., Ogawa K et al., 2000, Oncogene 19:6043-6052). Xenografts are typically implanted SC into female athymic mice, 6-7 week old, as single cell suspensions either from a preexisting tumor or from in vitro culture. The tumors which express the C20ORF23 endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan-D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific C20ORF23-modulating agents are useful in a variety of diagnostic and therapeutic applications where disease or disease prognosis is related to defects in the IGFR pathway, such as angiogenic, apoptotic, or cell proliferation disorders. Accordingly, the invention also provides methods for modulating the IGFR pathway in a cell, preferably a cell pre-determined to have defective or impaired IGFR function (e.g. due to overexpression, underexpression, or misexpression of IGFR, or due to gene mutations), comprising the step of administering an agent to the cell that specifically modulates C20ORF23 activity. Preferably, the modulating agent produces a detectable phenotypic change in the cell indicating that the IGFR function is restored. The phrase "function is restored", and equivalents, as used herein, means that the desired phenotype is achieved, or is brought closer to normal compared to untreated cells. For example, with restored IGFR function, cell proliferation and/or progression through cell cycle may normalize, or be brought closer to normal relative to untreated cells. The invention also provides methods for treating disorders or disease associated with impaired IGFR function by administering a therapeutically effective amount of a C20ORF23-modulating agent that modulates the IGFR pathway. The invention further provides methods for modulating C20ORF23 function in a cell, preferably a cell predetermined to have defective or impaired C20ORF23 function, by administering a C20ORF23-modulating agent. Additionally, the invention provides a method for treating disorders or disease associated with impaired C20ORF23 function by administering a therapeutically effective amount of a C20ORF23-modulating agent.

The discovery that C20ORF23 is implicated in IGFR pathway provides for a variety of methods that can be employed for the diagnostic and prognostic evaluation of diseases and disorders involving defects in the IGFR pathway and for the identification of subjects having a predisposition to such diseases and disorders.

Various expression analysis methods can be used to diagnose whether C20ORF23 expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147, Blohm and Guiseppi-Elie, Curr Opin Biotechnol 2001, 12:41-47). Tissues having a disease or disorder implicating defective IGFR signaling that express a C20ORF23, are identified as amenable to treatment with a C20ORF23 modulating agent. In a preferred application, the IGFR defective tissue overexpresses a C20ORF23 relative to normal tissue. For example, a Northern blot analysis of mRNA from tumor and normal cell lines, or from tumor and matching normal tissue samples from the same patient, using full or partial C20ORF23 cDNA sequences as probes, can determine whether particular tumors express or overexpress C20ORF23. Alternatively, the TAQMAN® is used for quantitative RT-PCR analysis of C20ORF23 expression in cell lines, normal tissues and tumor samples (PE APPLED BIOSYSTEMS).

Various other diagnostic methods may be performed, for example, utilizing reagents such as the C20ORF23 oligonucleotides, and antibodies directed against a C20ORF23, as described above for: (1) the detection of the presence of C20ORF23 gene mutations, or the detection of either over- or under-expression of C20ORF23 mRNA relative to the non-disorder state; (2) the detection of either an over- or an under-abundance of C20ORF23 gene product relative to the non-disorder state; and (3) the detection of perturbations or abnormalities in the signal transduction pathway mediated by C20ORF23.

Kits for detecting expression of C20ORF23 in various samples, comprising at least one antibody specific to C20ORF23, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in C20ORF23 expression, the method comprising: a) obtaining a biological sample from the patient; b) contacting the sample with a probe for C20ORF23 expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. Drosophila IGFR Screen

A dominant loss of function screen was carried out in Drosophila to identify genes that interact with or modulate the IGFR signaling pathway. Activation of the pathway by overexpression of IGFR at early stages in the developing Drosophila eye leads to an increase in cell number which results in a larger and rougher adult eye (Potter C J et al. (2001) Cell 105:357-368; Huang et al., 1999. Dev. 126:5365-5372). We generated a fly stock with an enlarged eye due to overexpression of IGFR and identified modifiers of this phenotype. We then identified human orthologues of these modifiers.

The screening stock carried two transgenes. The genotype is as follows:

+; +; P{DmIGFR-pExp-UAS)}P{Gal4-pExp-1Xey}/TM6B

Screening stock females of the above genotype were crossed to males from a collection of 3 classes of piggyBac-based transposons. The resulting progeny, which contain both the transgenes and the transposon, were scored for the effect of the transposon on the eye overgrowth phenotype (either enhancement, suppression or no effect). All data was recorded and all modifiers were retested with a repeat of the original cross. Modifiers of the eye phenotype were identified as members of the IGFR pathway. KLP98A was a suppressor of the eye phenotype. C20ORF23 is the ortholog of KLP98A.

BLAST analysis (Altschul et al., supra) was employed to identify orthologs of Drosophila modifiers. For example, representative sequences from C20ORF23, GI# 28395029 (SEQ ID NO:6) shares 47% amino acid identity with the Drosophila KLP98A.

Various domains, signals, and functional subunits in proteins were analyzed using the PSORT (Nakai K, and Horton P., Trends Biochem Sci, 1999, 24:346; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the Caenorhabditis elegans genome and identification of human orthologs. Genome Res. 2000 November; 10(11):1679-89) programs. For example, the kinesin motor domain (PFAM 00225) of C20ORF23 from GI# 28395029 (SEQ ID NO:6) is located at approximately amino acid residues 9 to 359.

II. High-Throughput In Vitro Binding Assay.

$^{33}$P-labeled C20ORF23 peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate IGFR modulating agents.

III. Immunoprecipitations and Immunoblotting

For coprecipitation of transfected proteins, 3×10$^6$ appropriate recombinant cells containing the C20ORF23 proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

IV. Expression Analysis

All cell lines used in the following experiments are NCI (National Cancer Institute) lines, and are available from ATCC$^{SM}$ (American Type Culture Collection, Manassas, Va. 20110-2209). Normal and tumor tissues were obtained from Impath, UC Davis, CLONTECH™, STRATAGENE®, Ardais, Genome Collaborative, and AMBION®.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of APPLIED BIOSYSTEMS® (Foster City, Calif.).

Primers for expression analysis using TAQMAN® assay (APPLIED BIOSYSTEMS®, Foster City, Calif.) were prepared according to the TAQMAN® protocols, and the following criteria: a) primer pairs were designed to span introns to eliminate genomic contamination, and b) each primer pair produced only one product. Expression analysis was performed using a 7900HT instrument.

TAQMAN® reactions were carried out following manufacturer's protocols, in 25 µl total volume for 96-well plates and 10 µl total volume for 384-well plates, using 300 nM primer and 250 nM probe, and approximately 25 ng of cDNA.

The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| Gene Name | C20orf23 (SEQ ID NO: 2) |
|---|---|
| Breast | 36% |
| # of Pairs | 36 |
| Colon | 45% |
| # of Pairs | 40 |
| Head And Neck | 31% |
| # of Pairs | 13 |
| Liver | 67% |
| # of Pairs | 9 |
| Lung | 22% |
| # of Pairs | 40 |
| Lymphoma | 0% |
| # of Pairs | 4 |
| Ovary | 0% |
| # of Pairs | 19 |
| Pancreas | 50% |
| # of Pairs | 12 |
| Prostate | 12% |
| # of Pairs | 24 |
| Skin | 43% |
| # of Pairs | 7 |
| Stomach | 27% |
| # of Pairs | 11 |
| Testis | 0% |
| # of Pairs | 8 |
| Thyroid Gland | 21% |
| # of Pairs | 14 |
| Uterus | 17% |
| # of Pairs | 23 |

V. C20ORF23 Functional Assays

RNAi experiments were carried out to knock down expression of C20ORF23 (SEQ ID NO:2) in various cell lines using small interfering RNAs (siRNA, Elbashir et al, supra).

Effect of C20ORF23 RNAi on cell proliferation and growth. BrdU and Cell TITERGLO™ assays, as described above, were employed to study the effects of decreased C20ORF23 expression on cell proliferation. The results of these experiments indicated that RNAi of C20ORF23 decreases proliferation in 231T breast cancer cells, A549 lung cancer cells, PC3 prostate cancer cells, and U87MG glioblastoma cells.

Standard colony growth assays, as described above, were employed to study the effects of decreased C20ORF23 expression on cell growth. The results of this experiment indicated that RNAi of C20ORF23 decreased cell count in A2780 ovarian cancer cells and 231T, A549, and PC3 cells.

[$^3$H]-thymidine incorporation assay, as described above, was also employed to study the effects of decreased C20ORF23 expression on cell proliferation. The results of this experiment indicated that RNAi of C20ORF23 decreased proliferation in RD1 rhabdomyosarcoma and A549 cells.

Effect of C20ORF23 RNAi on apoptosis. The Phospho-histone H2B assay, as described above, was also employed to study the effects of decreased C20ORF23 expression on apoptosis. The results of this experiment indicated that RNAi of C20ORF23 increased apoptosis in 231T and U87MG cells.

Multiple parameter apoptosis assay, as described above, was also used to study the effects of decreased C20ORF23 expression on apoptosis. The results of this experiment indicated that RNAi of C20ORF23 increased apoptosis in A2780 and A549 cells.

C20ORF23 FOXO nuclear translocation assays. FOXO nuclear translocation assays, as described above, were employed to assess involvement of C20ORF23 in the PTEN/IGF pathway. Results indicated that reduced expression of C20ORF23 led to retention of FOXO in the nucleus in U20S osteosarcoma, PC3, and A2780 cells. These results suggest involvement of C20ORF23 in the IGFR pathway.

Pan-AKT assays. This assay was developed to detect involvement of C20ORF23 in the PTEN/IGF pathway. The assay detects changes in phosphorylation for several substrates of AKT, such as PRAS40, BAD, 4EBP1, and RPS6. For this experiment, antibodies were raised against phosphorylated AKT substrates, including the consensus phosphorylated AKT substrate sequence RxRxxS/T. Expression levels of phosphorylated substrates were then quantitated at normal levels, in presence of a negative control, a positive control (AKT), and then with C20ORF23 knockout. For example, when AKT levels were reduced, expression of all its substrates was also reduced. Further, reduced expression of C20ORF23 caused a decrease in the levels of phospho AKT substrates in 231T and A549 cells.

We used RPS6 assay for one subset of experiments. RPS6 is an IGF dependent substrate of AKT. IGF1 treatment increases cytoplasmic RPS6 levels. Alternatively, Lily compound LY294002, a PI3K inhibitor, reduces AKT and cytoplasmic RPS6 levels. Cells were plated in 96 well plates, transfected with RNAi for C20ORF23, fixed, treated with RPS6 antibody, and stained. Measurements were based on percentage of population of cells with increased or decreased staining compared with negative or positive control cells. Results of this experiment showed that reduced expression of C20ORF23 caused a reduction in the level of phospho RPS6 protein in 231T cells, thus suggesting an involvement in the IGFR pathway.

We used 4EBP1 as the substrate for another subset of the experiments. For this substrate, AKT pathway inhibition causes decreased cytoplasmic staining and increased nuclear staining. Cells were plated in 96 well plates, transfected with RNAi for C20ORF23, fixed, treated with 4EBP1 antibody, and stained. Measurements were based on percentage of population of cells with increased or decreased nuclear/cytoplasmic staining ratio compared with negative or positive control cells. Results of this experiment showed that reduced expression of C20ORF23 caused a reduction in the level of phospho 4EBP1 protein in PC3 and A549 cells, thus suggesting an involvement in the IGFR pathway.

We used PRAS40 as the substrate for yet another subset of experiments. For this substrate, pathway inhibition causes decreased cytoplasmic staining and increased nuclear and perinuclear staining. Cells were plated in 96 well plates, transfected with RNAi for C20ORF23, fixed, treated with PRAS40 antibody, and stained. Measurements were based on percentage of population of cells with increased or decreased nuclear/cytoplasmic staining ratio compared with negative or positive control cells. Results of this experiment showed that reduced expression of C20ORF23 caused a reduction in the level of phospho PRAS40 protein in 231T cells, thus suggesting an involvement in the IGFR pathway.

High Throughput PTEN/IGFR Transcriptional readout assay. This assay is an expanded TaqMan® transcriptional readout assay monitoring changes in the mRNA levels of endogenous PTEN/IGF regulated genes. This assay measures changes in expression of PTEN/IGF regulated cellular genes as a readout for pathway signaling activity.

We identified a panel of genes that were transcriptionally regulated by PTEN/IGF signaling, then designed and tested TaqMan® primer/probes sets. We reduced expression of PTEN/IGF by RNAi, and tested its affect on the expression of the transcriptionally regulated genes in multiple cell types. The panel readout was then narrowed to the ten most robust probes.

We then treated cancer cells with siRNAs of the target genes of interest, such as C20ORF23, and tested how the reduced levels of the target genes affected the expression levels of the PTEN/IGF regulated gene panel.

Genes that when knocked out via at least 2 different RNAi oligos, demonstrated the same pattern of activity on at least one third of the panel genes as a PTEN/IGF knockout, were identified as involved in the PTEN/IGF pathway.

TaqMan® assays were performed on the RNAs in a 384 well format.

RNAi of C20ORF23 in 231T and PC3 cells showed the same pattern of activity as PTEN/IGF RNAi for at least 2 RNAi oligos on at least one third of the transcriptionally regulated genes.

What is claimed is:

1. A method of identifying a candidate Insulin-Like Growth Factor Receptor (IGFR) pathway modulating agent, said method comprising the steps of:
    (a) providing an assay system comprising cultured cells that express Chromosome 20 Open reading Frame 23 (C20ORF23) nucleic acid, wherein the C20ORF23 nucleic acid comprises SEQ ID NO: 2;
    (b) contacting the assay system with a test agent that modulates the expression of C20ORF23; and
    (c) detecting a change in the assay system in the presence of the test agent of step (b) as compared to the absence of the test agent, wherein the detection of a change in the assay system identifies the test agent as a candidate IGFR pathway modulating agent.

2. The method of claim 1, wherein the cultured cells have defective IGFR function.

3. The method of claim 1, wherein the assay system is selected from the group consisting of an apoptosis assay system, a cell proliferation assay system, an angiogenesis assay system, and a hypoxic induction assay system.

4. The method of claim 1, wherein the test agent is a nucleic acid modulator.

5. The method of claim 4, wherein the nucleic acid modulator is an antisense oligomer.

6. The method of claim 4, wherein the nucleic acid modulator is a phosphothioate morpholino oligomer (PMO).

7. The method of claim 1, comprising the additional steps of:
    (d) providing a second assay system capable of detecting a change in the IGFR pathway wherein the second assay system comprises cultured cells that express a C20ORF23 nucleic acid,
    (e) contacting the second assay system with the test agent of (b); and
    (f) determining a change in the IGFR pathway in the second assay system, wherein a change in the IGFR pathway in the presence of said test agent as compared to the absence of said test agent confirms the test agent as a candidate IGFR pathway modulating agent.

* * * * *

SEQUENCE LISTING

<160> NUMBER OF SEQ ID NOS: 6

<210> SEQ ID NO 1

<211> LENGTH: 5161
<212> TYPE: DNA
<213> ORGANISM: Homo sapiens

<400> SEQUENCE: 1

```
ggcaggtggg gccgccgcgg aactccaggt ccggccggga gcagaggggc ggggggcgaga      60
gggaagtggg cgggagccgc gatctgagta gccagcgtcg ccggcgaccg cggagttctg     120
ggctagtggg accccgcgcg ggctggttcg ggatgagcga tggcatcggt caaggtggcc     180
gtgagggtcc ggcccatgaa tcgcagggaa aaggacttgg aggccaagtt cattattcag     240
atggagaaaa gcaaaacgac aatcacaaac ttaaagatac cagaaggagg cactggggac     300
tcaggaagag aacggaccaa gaccttcacc tatgactttt cttttttattc tgctgataca     360
aaaagcccag attacgtttc acaagaaatg gttttcaaaa ccctcggcac agatgtcgtg     420
aagtctgcat ttgaaggtta taatgcttgt gtctttgcat atgggcaaac tggatctgga     480
aagtcataca ctatgatggg aaattctgga gattctggct taatacctcg gatctgtgaa     540
ggactcttca gtcggataaa tgaaaccacc agatgggatg aagcttcttt tcgaactgaa     600
gtcagctact tagaaatttta taacgaacgt gtgagagatc tacttcggcg gaagtcatct     660
aaaaccttca atttgagagt ccgtgagcat cccaaagaag gcccttatgt tgaggattta     720
tccaaacatt tagtacagaa ttatggtgac gtagaagaac ttatggatgc gggcaatatc     780
aaccggacca ccgcagcgac tgggatgaac gacgtcagta gcaggtctca tgccatcttc     840
accatcaagt tcactcaggc taaatttgat tctgaaatgc catgtgaaac cgtcagtaag     900
atccacttgg ttgatcttgc cggaagtgag cgtgcagatg ccaccggagc caccggggtt     960
aggctaaagg aaggggggaaa tattaacaag tccctcgtga ctctggggaa cgtcatttct    1020
gccttagctg atttatctca ggatgctgca aatactcttg caaagaagaa gcaagttttc    1080
gtgccttaca gggattctgt gttgacttgg ttgttaaaag atagccttgg aggaaactct    1140
aaaactatca tgattgccac catttcacct gctgatgtca attatggaga aaccctaagt    1200
actcttcgct atgcaaatag agccaaaaac atcatcaaca agcctaccat taatgaggat    1260
gccaacgtca aacttatccg tgagctgcga gctgaaatag ccagactgaa aacgctgctt    1320
gctcaaggga atcagattgc cctcttagac tcccccacag ctttaagtat ggaggaaaaa    1380
cttcagcaga atgaagcaag agttcaagaa ttgaccaagg aatggacaaa taagtggaat    1440
gaaacccaaa atattttgaa agaacaaact ctagccctca ggaaagaagg gattggagtt    1500
gttttggatt ctgaactgcc tcatttgatt ggcatcgatg atgacctttt gagtactgga    1560
atcatcttat atcatttaaa ggaaggtcag acatacgttg gtagagacga tgcttccacg    1620
gagcaagata ttgttcttca tggccttgac ttggagagtg agcattgcat ctttgaaaat    1680
atcgggggga cagtgactct gataccctg agtgggtccc agtgctctgt gaatggtgtt    1740
cagatcgtgg aggccacaca tctaaatcaa ggtgctgtga ttctcttggg aagaaccaat    1800
atgtttcgct ttaaccatcc aaaggaagcc gccaagctca gggagaagag gaagagtggc    1860
cttctgtcct ccttcagctt gtccatgacc gacctctcga agtcccgtga gaacctgtct    1920
gcagtcatgt tgtataaccc cggacttgaa tttgagaggc aacagcgtga agaacttgaa    1980
aaattagaaa gtaaaaggaa actcatagaa gaaatggagg aaaagcagaa atcagacaag    2040
gctgaactgg agcggatgca gcaggaggtg gagacccagc gcaaggagac agaaatcgtg    2100
cagctccaga ttcgcaagca ggaggagagc ctcaaacgcc gcagcttcca catctagaac    2160
aagctaaagg atttacttgc ggagaaggaa aaatttgaag aggagaggct gagggaacag    2220
```

```
caggaaatcg agctgcagaa gaagagacaa gaagaagaga cctttctccg cgtccaagaa    2280
gaactccaac gactcaaaga actcaacaac aacgagaagg ctgagaagtt tcagatattt    2340
caagaactgg accagctcca aaaggaaaaa gatgaacagt atgccaagct tgaactggaa    2400
aaaaagagac tagaggagca ggagaaggag caggtcatgc tcgtggccca tctggaagag    2460
cagctccgag agaagcagga gatgatccag ctcctgcggc gtgggaggt acagtgggtg     2520 gaagaggaga gagggacct ggaaggcatt cgggaatccc tcctgcgggt gaaggaggct     2580
cgtgccggag gggatgaaga tggcgaggag ttagaaaagg ctcaactgcg tttcttcgaa    2640
ttcaagagaa ggcagcttgt caagctagtg aacttggaga aggacctggt tcagcagaaa    2700
gacatcctga aaaagaagt ccaagaagaa caggagatcc tagagtgttt aaaatgtgaa     2760
catgacaaag aatctagatt gttggaaaaa catgatgaga gtgtcacaga tgtcacggaa    2820
gtgcctcaag atttcgagaa aataaagcca gtggagtaca ggctgcaata taagaacgc    2880 cagctacagt acctcctgca gaatcacttg ccaactctgt tggaagaaaa gcagagagca    2940
tttgaaattc ttgacagagg ccctctcagc ttagacaaca ctctttatca agtagaaaag    3000
gaaatggaaa aaaagaaga acagcttgca cagtaccagg ccaatgcaaa ccagctgcaa    3060
aagctccaag ccacctttga attcactgcc aacattgcac gtcaggagga aaaagtgagg    3120
aaaaaggaaa aggagatttt ggagtccaga gagaagcagc agagagaggc gctggagcgg   3180
gccctggcca ggctggagag gagacattct gcgctgcaga ggcactccac cctgggcacg    3240
gagattgaag agcagaggca gaaacttgcc agtctgaaca gtggcagcag agagcagtca    3300
gggctccagg ctagcctgga ggctgagcag gaagccctgg agaaggacca ggagaggatc    3360
aatgcttaca ttgaagaaga agtccaaaga cgccttcagg atttgcatcg tgtgattagt    3420
gaaggctgca gtacatctgc agacacgatg aaggataatg agaaacttca caatggcacc    3480
attcaacgta aactaaaata tgagcggatg gtttctcgct cttgggcgc aaatccagat    3540 gacctgaagg acccaattaa aattagtatc ccacgctacg tcctctgcgg gcaaggaaag    3600
gatgcacact tcgagtttga ggtcaagatt actgtcctag atgagacatg gactgtattc    3660
aggcgttaca gtcgttttcg agaaatgcat aaaacattga agttaaagta tgcagagctt    3720
gctgcccttg aatttcctcc aaagaaacta tttggaaata aggatgaacg tgtgattgct    3780
gagagacgaa gtcacttaga gaaatacctc agggacttt tcagcgtgat gctccagtcc    3840
gcaacatctc ccctccacat caacaaagtg ggactgactc tctcgaaaca taccatttgt    3900
gagttttcac cattcttcaa gaaagggagtc tttgactaca gcagccacgg gacggggtag   3960
agccaggggt gatggaggaa ccaccacagc agtgccttct cgtcgaagcg ggctccgatg    4020
cagggcagct cccccatgcg aggatccggg tctgcctcct cctgctgaag acagacatgc    4080
agcagcgggc ccgggccacc tcacgtttcc atacctagtg cctgagtttg gggatgggat    4140
gctctgcctg ctgatgtggc cctgacaggc agccgttacc gttccattgc ggttgaacgt    4200
ggccttttcc cacagtgctt ccttctcact gcgcagcaaa gttcgtcccc tgtggcaaga    4260
tagatgtggt tgggccatcg tgggttccct gagcccagcc agcctgggac ctcccaaagt    4320
gggtggctta ccagaccacc cttaaatgac tttcatctgg tttcctcttt caccaaaata    4380
tactcgtatt ttttatattt cttccatgtg gctggctata ttccaagaaa agcattttaa    4440
attatttcat tgtattttt ctttttttc cctcatttga atcagaactt ttatataaaa     4500
cccaaacact gatgtttaca cagaatttca tattctgcaa aagggattt ttgatccaat    4560 catgactgta gtcttccatg cttgacaaat tggatgtaga caacattact taaaacttct   4620
```

-continued

| | |
|---|---|
| ataaatccct acaattagga tatttattta accttgaata ttcaagaaca ttctcccaaa | 4680 |
| tctaaatggc tactgtgcat tcttgagctt tttctgctaa gcacaaaatg aacgcaaagc | 4740 |
| taaatgcata tttttaagta ttattcacat tttttgttac agaatctatt ggatctttgg | 4800 |
| ctggaaaact agaatttata gcagtttatt aatgataccT taaattactc aggacttaat | 4860 |
| gtagcattgc acttctgtgt acagtaaaac tgctttgttt tactaaagag aaaaatgtga | 4920 |
| gtggaaaaaa tatgtatgtg ttatatactc aaatgtatat aattctatct atagatttat | 4980 |
| atatgtatac attctgtaca gtagttccat caaaatatgt aataattcac accaatttta | 5040 |
| ttaaatgtat ttgcttttc aaaatttaaa ttgagctgct atcaatatta aatgaagtta | 5100 |
| tggcatctaa aaaaaaaaaa aaaaaaaaa aaaaaaaaa aaaaaaaaa aaaaaaaaaa | 5160 |
| a | 5161 |

<210> SEQ ID NO 2
<211> LENGTH: 5282
<212> TYPE: DNA
<213> ORGANISM: Homo sapiens

<400> SEQUENCE: 2

| | |
|---|---|
| gcaggtgggg ccgccgcgga actccaggtc cggccgggag cagaggggcg ggggcgagag | 60 |
| ggaagtgggc gggagccgcg atctgagtag ccagcgtcgc cggcgaccgc ggagttctgg | 120 |
| gctagtggga ccccgcgcgg gctggttcgg gatgagcgat ggcatcggtc aaggtggccg | 180 |
| tgagggtccg gcccatgaat cgcagggaaa aggacttgga ggccaagttc attattcaga | 240 |
| tggagaaaag caaaacgaca atcacaaact taaagatacc agaaggaggc actggggact | 300 |
| caggaagaga acggaccaag accttcacct atgacttttc ttttattct gctgatacaa | 360 |
| aaagcccaga ttacgtttca caagaaatgg ttttcaaaac cctcggcaca gatgtcgtga | 420 |
| agtctgcatt tgaaggttat aatgcttgtg tctttgcata tgggcaaact ggatctggaa | 480 |
| agtcatacac tatgatggga aattcaggag attctggctt aatacctcgg atctgtgaag | 540 |
| gactcttcag tcggataaat gaaaccacca gatgggatga agcttctttt cgaactgaag | 600 |
| tcagctactt agaaatttat aacgaacgtg tgagagatct acttcggcgg aagtcatcta | 660 |
| aaaccttcaa tttgagagtc cgtgagcatc ccaagaagg cccttatgtt gaggatttat | 720 |
| ccaaacattt agtacagaat tatggtgacg tagaagaact tatggatgcg ggcaatatca | 780 |
| accggaccac cgcagcgact gggatgaacg acgtcagtag caggtctcat gccatcttca | 840 |
| ccatcaagtt cactcaggct aaatttgatt ctgaaatgcc atgtgaaacc gtcagtaaga | 900 |
| tccacttggt tgatcttgcc ggaagtgagc gtgcagatgc caccggagcc accggggtta | 960 |
| ggctaaagga agggggaaat attaacaagt cccttgtgac tctggggaac gtcatttctg | 1020 |
| ccttagctga tttatctcag gatgctgcaa atactcttgc aaagaagaag caagttttcg | 1080 |
| tgccttacag ggattctgtg ttgacttggt tgttaaaaga tagccttgga ggaaactcta | 1140 |
| aaactatcat gattgccacc atttcacctg ctgatgtcaa ttatggagaa accctaagta | 1200 |
| ctcttcgcta tgcaaataga gccaaaaaca tcatcaacaa gcctaccatt aatgaggatg | 1260 |
| ccaacgtcaa acttatccgt gagctgcgag ctgaaatagc cagactgaaa acgctgcttg | 1320 |
| ctcaagggaa tcagattgcc ctcttagact cccccacagc tttaagtatg gaggaaaaac | 1380 |
| ttcagcagaa tgaagcaaga gttcaagaat tgaccaagga atggacaaat aagtggaatg | 1440 |
| aaacccaaaa tattttgaaa gaacaaactc tagccctcag gaaagaaggg attggagttg | 1500 |
| ttttggatc tgaactgcct catttgattg gcatcgatga tgaccttttg agtactggaa | 1560 |

```
tcatcttata tcatttaaag gaaggtcaga catacgttgg tagagacgat gcttccacgg   1620
agcaagatat tgttcttcat ggccttgact tggagagtga gcattgcatc tttgaaaata   1680 tcgggggac  agtgactctg ataccctga  gtgggtccca gtgctctgtg aatggtgttc   1740
agatcgtgga ggccacacat ctaaatcaag gtgctgtgat tctcttggga agaaccaata   1800
tgtttcgctt taaccatcca aggaagccg  ccaagctcag ggagaagagg aagagtggcc   1860
ttctgtcctc cttcagcttg tccatgaccg acctctcgaa gtcccgtgag aacctgtctg   1920
cagtcatgtt gtataacccc ggacttgaat ttgagaggca acagcgtgaa gaacttgaaa   1980
aattagaaag taaaggaaa  ctcatagaag aaatggagga aaagcagaaa tcagacaagg   2040
ctgaactgga gcggatgcag caggaggtgg agacccagcg caaggagaca gaaatcgtgc   2100
agctccagat tcgcaagcag gaggagagcc tcaaacgccg cagcttccac atcgagaaca   2160
agctaaagga tttacttgcg gagaaggaaa aatttgaaga ggagaggctg agggaacagc   2220
aggaaatcga gctgcagaag aagagacaag aagaagagac cttctctccgc gtccaagaag   2280 aactccaacg actcaaagaa ctcaacaaca acgagaaggc tgagaagttt cagatatttc   2340
aagaactgga ccagctccaa aaggaaaaag atgaacagta tgccaagctt gaactggaaa   2400
aaaagagact agaggagcag gagaaggagc aggtcatgct cgtggcccat ctggaagagc   2460
agctccgaga gaagcaggag atgatccagc tcctgcggcg tggggaggta cagtgggtgg   2520
aagaggagaa gagggacctg gaaggcattc gggaatccct cctgcgggtg aaggaggctc   2580
gtgccggagg ggatgaagat ggcgaggagt tagaaaaggc tcaactgcgt ttcttcgaat   2640
tcaagagaag gcagcttgtc aagctagtga acttggagaa ggacctggtt cagcagaaag   2700
acatcctgaa aaaagaagtc caagaagaac aggagatcct agagtgttta aaatgtgaac   2760
atgacaaaga atctagattg ttggaaaaac atgatgagag tgtcacagat gtcacggaag   2820
tgcctcaaga tttcgagaaa ataaagccag tggagtacag gctgcaatat aaagaacgcc   2880
agctacagta cctcctgcag aatcacttgc caactctgtt ggaagaaaag cagagagcat   2940
ttgaaattct tgacagaggc cctctcagct tagacaacac tctttatcaa gtagaaaagg   3000
aaatggaaga aaaagaagaa cagccttgcac agtaccaggc caatgcaaac cagctgcaaa   3060
agctccaagc caccttttgaa ttcactgcca acattgcacg tcaggaggaa aaagtgagga   3120
aaaaggaaaa ggagattttg gagtccagag agaagcagca gagagaggcg ctggagcggg   3180
ccctggccag gctggagagg agacattctg cgctgcagag gcactccacc ctgggcatgg   3240
agattgaaga gcagaggcag aaacttgcca gtctgaacag tggcagcaga gagcagtcag   3300
ggctccaggc tagcctggag gctgagcagg aagccctgga aaggaccag  gagaggttag   3360 aatatgaaat ccagcagctg aaacagaaga tttatgaggt cgatggtgtt caaaaagatc   3420
atcatgggac cctggaaggg aaggtggctt cttccagctt gccagtcagt gctgaaaaat   3480
cacacctggt tcccctcatg gatgccagga tcaatgctta cattgaagaa gaagtccaaa   3540
gacgccttca ggatttgcat cgtgtgatta gtgaaggctg cagtacatct gcagacacga   3600
tgaaggataa tgagaaactt cacaatgcca ccattcaacg taaactaaaa tatgagcgga   3660
tggtttctcg ctcttttggg gcaaatccag atgacctgaa ggacccaatt aaaattagta   3720
tcccacgcta cgtcctctgc gggcaaggaa aggatgcaca cttcgagttt gaggtcaaga   3780
ttactgtcct agatgagaca tggactgtat tcaggcgtta cagtcgtttt cgagaaatgc   3840
ataaaacatt gaagttaaag tatgcagagc ttgctgccct tgaatttgct ccaaagaaac   3900
tatttggaaa taaggatgaa cgtgtgattg ctgagagacg aagtcactta gagaaatacc   3960
```

-continued

```
tcagggactt tttcagcgtg atgctccagt ccgcaacatc tccccctccac atcaacaaag    4020 tgggactgac tctctcgaaa cataccattt gtgagttttc accattcttc aagaaaggag    4080
tctttgacta cagcagccac gggacggggt agagccagga gtgatggagg aaccaccaca    4140
gcagtgcctt ctcgtcgaag cgggctccga tgcagggcag ctcccccatg cgaggatccg    4200
ggtctgcctc ctcctgctga agacagacat gcagcagcgg gcccgggcca cctcacgttt    4260
ccatacctag tgcctgagtt tggggatggg atgctctgcc tgctgatgtg gccctgacag    4320
gcagccgtta ccgttccatt gcggttgaac gtggccttt cccacagtgc ttccttctca    4380
ctgcgcagca aagttcgtcc cctgtggcaa gatagatgtg gttgggccat cgtgggttcc    4440
ctgagcccag ccagcctggg acctcccaaa gtgggtggct taccagacca cccttaaatg    4500
actttcatct ggtttcctct ttcaccaaaa tatactcgta tttttatat ttcttccatg    4560 tggctggcta tattccaaga aaagcatttt aaattatttc attgtatttt tttctttttt    4620
tccctcattt gaatcagaac ttttatataa aacccaaaca ctgatgttta cacagaattt    4680
catattctgc aaaagggatt ttttgatcca atcatgactg tagtcttcca tgcttgacaa    4740
attggatgta gacaacatta cttaaaactt ctataaatcc ctacaattag gatatttatt    4800
taaccttgaa tattcaagaa cattctccca aatctaaatg gctactgtgc attcttgagc    4860 ttttctgct aagcacaaaa tgaacgcaaa gctaaatgca tattttaag tattattcac    4920 attttttgtt acagaatcta ttggatcttt ggctggaaaa ctagaatta tagcagttta    4980 ttaatgatac cttaaattac tcaggactta atgtagcatt gcacttctgt gtacagtaaa    5040
actgctttgt tttactaaag agaaaaatgt gagtggaaaa aatatgtatg tgttatatac    5100
tcaaatgtat ataattctat ctatagattt atatatgtat acattctgta cagtagttcc    5160
atcaaaatat gtaataattc accaattttt tattaaatgt atttgctttt tcaaaattta    5220
aattgagctg ctatcaatat taaatgaagt tatggcatct aaaaaaaaaa aaaaaaaaa    5280 aa                                                                     5282
```

<210> SEQ ID NO 3
<211> LENGTH: 5215
<212> TYPE: DNA
<213> ORGANISM: Homo sapiens

<400> SEQUENCE: 3

```
atctgagtag ccagcgtcgc cggcgaccgc ggagttctgg gctagtggga ccccgcgcgg      60
gctggttcgg gatgagcgat ggcatcggtc aaggtggccg tgagggtccg gcccatgaat    120
cgcagggaaa aggacttgga ggccaagttc attattcaga tggagaaaag caaaacgaca    180
atcacaaact aaagatacc agaaggaggc actgggact caggaagaga acggaccaag    240
accttcacct atgactttc ttttatttct gctgatacaa aaagcccaga ttacgtttca    300
caagaaatgg ttttcaaaac cctcggcaca gatgtcgtga agtctgcatt tgaaggttat    360
aatgcttgtg tctttgcata tgggcaaact ggatctggaa agtcatacac tatgatggga    420
aattctggag attctggctt aatacctcgg atcgtgaag gactcttcag tcggataaat    480
gaaaccacca gatgggatga agcttctttt cgaactgaag tcagctactt agaaatttat    540
aacgaacgtg tgagagatct acttcggcgg aagtcatcta aaccttcaa tttgagagtc    600 cgtgagcatc ccaagaagg cccttatgtt gaggatttat ccaaacattt agtacagaat    660
tatggtgacg tagaagaact tatggatgcg ggcaatatca accggaccac cgcagcgact    720
gggatgaacg acgtcagtag caggtctcat gccatcttca ccatcaagtt cactcaggct    780
```

| | |
|---|---|
| aaatttgatt ctgaaatgcc atgtgaaacc gtcagtaaga tccacttggt tgatcttgcc | 840 |
| ggaagtgagc gtgcagatgc caccggagcc accggggtta ggctaaagga aggggagat | 900 |
| attaacaagt ccctcgtgac tctggggaac gtcatttctg ccttagctga tttatctcag | 960 |
| gatgctgcaa atactcttgc aaagaagaag caagttttcg tgccttacag ggattctgtg | 1020 |
| ttgacttggt tgttaaaaga tagccttgga ggaaactcta aaactatcat gattgccacc | 1080 |
| atttcacctg ctgatgtcaa ttatggagaa accctaagta ctcttcgcta tgcaaataga | 1140 |
| gccaaaaaca tcatcaacaa gcctaccatt aatgaggatg ccaacgtcaa acttatccgt | 1200 |
| gagctgcgag ctgaaatagc cagactgaaa acgctgcttg ctcaagggaa tcagattgcc | 1260 |
| ctcttagact cccccacagc tttaagtatg gaggaaaaac ttcagcagaa tgaagcaaga | 1320 |
| gttcaagaat tgaccaagga atggacaaat aagtggaatg aaacccaaaa tattttgaaa | 1380 |
| gaacaaactc tagccctcag gaaagaaggg attggagttg ttttggattc tgaactgcct | 1440 |
| catttgattg gcatcgatga tgaccttttg agtactggaa tcatcttata tcatttaaag | 1500 |
| gaaggtcaga catacgttgg tagagacgat gcttccacgg agcaagatat tgttcttcat | 1560 |
| ggccttgact ggagagtga gcattgcatc tttgaaaata tcggggggac agtgactctg | 1620 |
| ataccctga gtgggtccca gtgctctgtg aatggtgttc agatcgtgga ggccacacat | 1680 |
| ctaaatcaag gtgctgtgat tctcttggga agaaccaata tgtttcgctt taaccatcca | 1740 |
| aaggaagccg ccaagctcag ggagaagagg aagagtggcc ttctgtcctc cttcagcttg | 1800 |
| tccatgaccg acctctcgaa gtcccgtgag aacctgtctg cagtcatgtt gtataacccc | 1860 |
| ggacttgaat ttgagaggca acagcgtgaa gaacttgaaa aattagaaag taaaaggaaa | 1920 |
| ctcatagaag aaatggagga aaagcagaaa tcagacaagg ctgaactgga gcggatgcag | 1980 |
| caggaggtgg agacccagcg caaggagaca gaaatcgtgc agctccagat tcgcaagcag | 2040 |
| gaggagagcc tcaaacgccg cagcttccac atcgagaaca gctaaagga tttacttgcg | 2100 |
| gagaaggaaa aatttgaaga ggagaggctg agggaacagc aggaaatcga gctgcagaag | 2160 |
| aagagacaag aagaagagac ctttctccgc gtccaagaag aactccaacg actcaaagaa | 2220 |
| ctcaacaaca acgagaaggc tgagaagttt cagatatttc aagaactgga ccagctccaa | 2280 |
| aaggaaaaag atgaacagta tgccaagctt gaactggaaa aaagagact agaggagcag | 2340 |
| gagaaggagc aggtcatgct cgtggcccat ctggaagagc agctccgaga gaagcaggag | 2400 |
| atgatccagc tcctgcggcg tggggaggta cagtgggtgg aagaggagaa gagggacctg | 2460 |
| gaaggcattc gggaatccct cctgcgggtg aaggaggctc gtgccggagg ggatgaagat | 2520 |
| ggcgaggagt tagaaaaggc tcaactgcgt ttcttcgaat tcaagagaag gcagcttgtc | 2580 |
| aagctagtga acttggagaa ggacctggtt cagcagaaag acatcctgaa aaagaagtc | 2640 |
| caagaagaac aggagatcct agagtgttta aaatgtgaac atgacaaaga atctagattg | 2700 |
| ttggaaaaac atgatgagag tgtcacagat gtcacggaag tgcctcaaga tttcgagaaa | 2760 |
| ataaagccag tggagtacag gctgcaatat aaagaacgcc agctacagta cctcctgcag | 2820 |
| aatcacttgc caactctgtt ggaagaaaag cagagagcat ttgaaattct tgacagaggc | 2880 |
| cctctcagct tagacaacac tctttatcaa gtagaaaagg aaatggaaga aaagaagaa | 2940 |
| cagcttgcac agtaccaggc caatgcaaac cagctgcaaa agctccaagc caccttgaa | 3000 |
| ttcactgcca acattgcacg tcaggaggaa aaagtgagga aaaggaaaa ggagatttg | 3060 |
| gagtccagag agaagcagca gagagaggcg ctggagcggg ccctggccag gctggagagg | 3120 |
| agacattctg cgctgcagag gcactccacc ctgggcacgg agattgaaga gcagaggcag | 3180 |

```
aaacttgcca gtctgaacag tggcagcaga gagcagtcag ggctccaggc tagcctggag    3240
gctgagcagg aagccctgga gaaggaccag gagaggttag aatatgaaat ccagcagctg    3300
aaacagaaga tttatgaggt cgatggtgtt caaaaagatc atcatgggac cctggaaggg    3360
aaggtggctt cttccaactt gccagtcagt gctgaaaaat cacacctggt tccctcatg     3420
gatgccagga tcaatgctta cattgaagaa aagtccaaa gacgccttca ggatttgcat     3480
cgtgtgatta gtgaaggctg cagtacatct gcagacacga tgaaggataa tgagaaactt    3540
cacaatggca ccattcaacg taaactaaaa tatgagcgga tggtttctcg ctctttgggc    3600
gcaaatccag atgacctgaa ggacccaatt aaaattagta tcccacgcta cgtcctctgc    3660
gggcaaggaa aggatgcaca cttcgagttt gaggtcaaga ttactgtcct agatgagaca    3720
tggactgtat tcaggcgtta cagtcgtttt cgagaaatgc ataaaacatt gaagttaaag    3780
tatgcagagc ttgctgccct tgaatttcct ccaaagaaac tatttggaaa taaggatgaa    3840
cgtgtgattg ctgagagacg aagtcactta gagaaatacc tcagggactt tttcagcgtg    3900
atgctccagt ccgcaacatc tcccctccac atcaacaaag tgggactgac tctctcgaaa    3960
cataccattt gtgagttttc accattcttc aagaaaggag tctttgacta cagcagccac    4020
gggacggggt agagccaggg gtgatggagg aaccaccaca gcagtacctt ctcgtcgaag    4080
cgggctccga tgcagggcag ctccccccatg cgaggatccg ggtctgcctc ctcctgctga   4140
agacagacat gcagcagcgg gcccgggcca cctcacgttt ccatacctag tgcctgagtt    4200
tggggatggg atgctctgcc tgctgatgtg gccctgacag gcagccgtta ccgttccatt    4260
gcggttgaac gtggccttt cccacagtgc ttccttctca ctgcgcagca aagttcgtcc     4320
cctgtggcaa gatagatgtg gttgggccat cgtgggttcc ctgagcccag ccagcctggg    4380
acctcccaaa gtgggtggct taccagacca cccttaaatg actttcatct ggtttcctct    4440
ttcaccaaaa tatactcgta ttttatatt tcttccatgt ggctggctat attccaagaa     4500
aagcattta aattatttca ttgtatttt ttcttttttt ccctcatttg aatcagaact      4560
tttatataaa acccaaacac tgatgtttac acagaatttc atattctgca aaagggattt    4620
tttgatccaa tcatgactgt agtcttccat gcttgacaaa ttggatgtag acaacattac    4680
ttaaaacttc tataaatccc tacaattagg atatttattt aaccttgaat attcaagaac    4740
attctcccaa atctaaatgg ctactgtgca ttccttgagct ttttctgcta agcacaaaat   4800
gaacgcaaag ctaaatgcat attttttaagt attattcaca ttttttgtta cagaatctat   4860
tggatctttg gctggaaaac tagaatttat agcagtttat taatgatacc ttaaattact    4920
caggacttaa tgtagcattg cacttctgtg tacagtaaaa ctgctttgtt ttactaaaga    4980
gaaaaatgtg agtggaaaaa atatgtatgt gttatatact caaatgtata taattctatc    5040
tatagattta tatatgtata cattctgtac agtagttcca tcaaaatatg taataattca    5100
caccaatttt attaaatgta tttgcttttt caaaatttaa attgagctgc tatcaatatt    5160
aaatgaagtt atggcatcta aaaaaaaaa aagaaaaaa aaaaaaaaaa aaaaa           5215
```

<210> SEQ ID NO 4
<211> LENGTH: 4558
<212> TYPE: DNA
<213> ORGANISM: Homo sapiens

<400> SEQUENCE: 4

```
ctgagtagcc agcgtcgccg gcgaccgcgg agttctgggc tagtgggacc ccgcgcgggc      60
tggttcggga tgagcgatgg catcggtcaa ggtggccgtg agggtccggc ccatgaatcg     120
```

```
cagggaaaag gacttggagg ccaagttcat tattcagatg gagaaaagca aaacgacaat    180
cacaaactta aagataccag aaggaggcac tggggactca ggaagagaac ggaccaagac    240
cttcacctat gacttttctt tttattctgc tgatacaaaa agcccagatt acgtttcaca    300
agaaatggtt ttcaaaaccc tcggcacaga tgtcgtgaag tctgcatttg aaggttataa    360
tgcttgtgtc tttgcatatg ggcaaactgg atctggaaag tcatacacta tgatgggaaa    420
ttctggagat tctggcttaa tacctcggat ctgtgaagga ctcttcagtc ggataaatga    480
aaccaccaga tgggatgaag cttcttttcg aactgaagtc agctacttag aaatttataa    540
cgaacgtgtg agagatctac ttcggcggaa gtcatctaaa accttcaatt tgagagtccg    600
tgagcatccc aaagaaggcc cttatgttga ggatttatcc aaacatttag tacagaatta    660
tggtgacgta aagaactta tggatgcggg caatatcaac cggaccaccg cagcgactgg    720
gatgaacgac gtcagtagca ggtctcatgc catcttcacc atcaagttca ctcaggctaa    780
atttgattct gaaatgccat gtgaaaccgt cagtaagatc cacttggttg atcttgccgg    840
aagtgagcgt gcagatgcca ccggagccac cggggttagg ctaaaggaag ggggaaatat    900
taacaagtcc cttgtgactc tggggaacgt catttctgcc ttagctgatt tatctcagga    960
tgctgcaaat actcttgcaa agaagaagca agttttcgtg ccttacaggg attctgtgtt   1020
gacttggttg ttaaaagata gccttggagg aaactctaaa actatcatga ttgccaccat   1080
ttcacctgct gatgtcaatt atggagaaac cctaagtact cttcgctatg caaatagagc   1140
caaaaacatc atcaacaagc ctaccattaa tgaggatgcc aacgtcaaac ttatccgtga   1200
gctgcgagct gaaatagcca gactgaaaac gctgcttgct caagggaatc agattgccct   1260
cttagactcc cccacagctt taagtatgga ggaaaaactt cagcagaatg aagcaagagt   1320
tcaagaattg accaaggaat ggacaaataa gtggaatgaa acccaaaata ttttgaaaga   1380
acaaactcta gccctcagga agaagggat tggagttgtt ttggattctg aactgcctca   1440
tttgattggc atcgatgatg accttttgag tactggaatc atcttatatc atttaaagga   1500
aggtcagaca tacgttggta gagacgatgc ttccacggag caagatattg ttcttcatgg   1560
ccttgacttg gagagtgagc attgcatctt tgaaaatatc ggggggacag tgactctgat   1620
acccctgagt gggtcccagt gctctgtgaa tggtgttcag atcgtggagg ccacacatct   1680
aaatcaaggt gctgtgattc tcttgggaag aaccaatatg tttcgcttta accatccaaa   1740
ggaagccgcc aagctcaggg agaagaggaa gagtggcctt ctgtcctcct tcagcttgtc   1800
catgaccgac ctctcgaagt cccgtgagaa cctgtctgca gtcatgttgt ataacccgg   1860 acttgaatt gagaggcaac agcgtgaaga acttgaaaaa ttagaaagta aaggaaact   1920 catagaagaa atggaggaaa agcagaaatc agacaaggct gaactggagc ggatgcagca   1980
ggaggtggag acccagcgca aggagacaga atcgtgcag ctccagattc gcaagcagga   2040
ggagagcctc aaacgccgca gcttccacat cgagaacaag ctaaaggatt tacttgcgga   2100
gaaggaaaaa tttgaagagg agaggctgag ggaacagcag gaaatcgagc tgcagaagaa   2160
gagacaagaa gaagagacct ttctccgcgt ccaagaagaa ctccaacgac tcaaagaact   2220
caacaacaac gagaaggctg agaagtttca gatatttcaa gaactggacc agctccaaaa   2280
ggaaaaagat gaacagtatg ccaagcttga actggaaaaa aagagactag aggagcagga   2340
gaaggagcag gtcatgctcg tggcccatct ggaagagcag ctccgagaga agcaggagat   2400
gatccagctc ctgcggcgtg gggaggtaca gtgggtggaa gaggagaaga ggggacctgga   2460 aggcattcgg gaatccctcc tgcgggtgaa ggaggctcgt gccggagggg atgaagatgg   2520
```

```
cgaggagtta gaaaaggctc aactgcgttt cttcgaattc aagagaaggc agcttgtcaa    2580
gctagtgaac ttggagaagg acctggttca gcagaaagac atcctgaaaa aagaagtcca    2640
agaagaacag gagatcctag agtgtttaaa atgtgaacat gacaaagaat ctagattgtt    2700
ggaaaaacat gatgagagtg tcacagatgt cacggaagtg cctcaagatt tcgagaaaat    2760
aaagccagtg gagtacaggc tgcaatataa agaacgccag ctacagtacc tcctgcagaa    2820
tcacttgcca actctgttgg aagaaaagca gagagcattt gaaattcttg acagaggccc    2880
tctcagctta gacaacactc tttatcaagt agaaaaggaa atggaagaaa agaagaaaca    2940
gcttgcacag taccaggcca atgcaaacca gctgcaaaag ctccaagcca cctttgaatt    3000
cactgccaac attgcacgtc aggaggaaaa agtgaggaaa aaggaaaagg agattttgga    3060
gtccagagag aagcagcaga gagaggcgct ggagcgggcc ctggccaggc tggagaggag    3120
acattctgcg ctgcagaggc actccaccct gggcacggag attgaagagc agaggcagaa    3180
acttgccagt ctgaacagtg gcagcagaga gcagtcaggg ctccaggcta gcctggaggc    3240
tgagcaggaa gccctggaga aggaccagga gaggttagaa tatgaaatcc agcagctgaa    3300
acagaagatt tatgaggtcg atggtgttca aaaagatcat catgggaccc tggaagggaa    3360
ggtggcttct tccagcttgc cagtcagtgc tgaaaaatca cacctggttc ccctcatgga    3420
tgccaggatc aatgcttaca ttgaagaaga agtccaaaga cgccttcagg atttgcatcg    3480
tgtgattagt gaaggctgca gtacatctgc agacacgatg aaggataatg agaaacttca    3540
caatggcacc attcaacgta aactaaaata tgagctgtgt cgtgacctcc tgtgtgtcct    3600
gatgccagag cctgatgccg ctgcctgcgc taatcatccc ttgctccagc aagatctggt    3660 tcagcttttct cttgattgga aaacagaaat ccctgattta gttttgccaa atggagttca    3720
ggtgtcatcc aaattccaga ctaccttggt tgacatgatt tactttcttc atggaaatat    3780
ggaagtcaat gtcccttccc tggcagaagt tcagttactg ctctacacaa cagtgaaagt    3840
catgggtgac tctggccatg accagtgcca gtcgctagtc cttctgaaca cccacattgc    3900
actggtgaag gaagactgtg ttttttatcc acgcattcga tctcgaaaca tacctcctcc    3960
gggtgcacaa tttgatgtga tcaaatgcca tgctttaagt gaattcaggt gtgttgttgt    4020
tccagaaaag aaaaatgtgt caacagtaga actagtcttc ttacagaaac tcaaaccttc    4080
agtgggttcc agaaatagtc cacctgagca ccttcaggaa gccccaaatg tccagttgtt    4140
caccacccca ttgtatcttc aaggcagtca gaatgtcgca cctgaggtct ggaaacttac    4200
tttcaattct caagatgagg ctcttttggct aatctcacat ttgacaagac tctaaggagg    4260
agacttttaa agatgcacta catgtttttt gagatcatta ataaaataag cattgtgaaa    4320
acagtcaagg caatatgaat atctccgtgt agctaattga attggaactg gaaaaatgca    4380
gacctctaaa attgaaaatg taactatttt aaatatctac aataaaataa aaacagctaa    4440
tagcagagcc ccaatgaaat atctttatca tcaccttgct tcattttctt gaaactcagg    4500
cttgtaaatt tgtgcctgct tcattatttg tgaggtgatt aaagcatttc tgattgtt      4558

<210> SEQ ID NO 5
<211> LENGTH: 1863
<212> TYPE: DNA
<213> ORGANISM: Homo sapiens

<400> SEQUENCE: 5
agcgaggaag ccctggagaa ggaccaggag aggttagaat atgaaatcca gcagctgaaa      60
cagaagattt atgaggtcga tggtgttcaa aaagatcatc atgggaccct ggaagggaag     120
```

```
gtggcttctt ccagcttgcc agtcagtgct gaaaaattac acctggttcc cctcatggat       180
gccaggatca atgcttacat tgaagaagaa gtccaaagac gccttcagga tttgcatcgt       240
gtgattagtg aaggctgcag tacatctgca gacacgatga aggataatga gaaacttcac       300
aatggcacca ttcaacgtaa actaaaaatat gagcggatgt tttctcgctc tttgggcgca     360
aatccagatg acctgaagga cccaattaaa attagtatcc cacgctacgt cctctgcggg       420
caaggaaagg atgcacactt cgagtttgag gtcaagcttg ctgcccttga atttcctcca       480
aagaaactat ttggaaataa ggatgaacgt gtgattgctg agagacgaag tcacttagag       540
aaatacctca gggacttttt cagcgtgatg ctccagtccg caacatctcc cctccacatc       600
aacaaagtgg gactgactct ctcgaaacat accatttgtg agttttcacc attcttcaag       660
aaaggagtct ttgactacag cagccacggg acggggtaga gccaggggtg atggaggaac       720
caccacagca gtgccttctc gtcgaagcgg gctccgatgc agggcagctc ccccatgcga       780
ggatccgggt ctgcctcctc ctgctgaaga cagacatgca gcagcgggcc cgggccacct       840 cacgttttcca tacctagtgc ctgagtttgg ggatgggatg ctctgcctgc tgatgtggcc       900
ctgacaggca gccgttaccg ttccattgcg gttgaacgtg gccttttccc acagtgcttc       960
cttctcactg cgcagcaaag ttcgtcccct gtggcaagat agatgtggtt gggccatcgt      1020
gggttccctg agcccagcca gcctgggacc tcccaaagtg ggtggcttac cagaccaccc      1080
ttaaatgact ttcatctggt ttcctctttc accaaaatat actcgtattt tttatatttc      1140
ttccatgtgg ctggctatat tccaagaaaa gcattttaaa ttatttcatt gtatttttt       1200 cttttttttcc ctcatttgaa tcagaacttt tatataaaac ccaaacactg atgtttacac      1260
agaatttcat attctgcaaa agggattttt tgatccaatc atgactgtag tcttccatgc      1320
ttgacaaatt ggatgtagac aacattactt aaaacttcta taaatcccta caattaggat      1380
atttatttaa ccttgaatat tcaagaacat tctcccaaat ctaaatggct actgtgcatt      1440
cttgagcttt ttctgctaag cacaaaatga acgcaaagct aaatgcatat ttttaagtat      1500
tattcacatt ttttgttaca gaatctattg gatctttggc tggaaaacta gaatttatag      1560
cagtttatta atgatacctt aaattactca ggacttaatg tagcattgca cttctgtgta      1620
cagtaaaact gctttgtttt actaaagaga aaaatgtgag tggaaaaaat atgtatgtgg      1680
tatatactca aatgtatata attctatcta tagatttata tatgtataca ttctgtacag      1740
tagttccatc aaaatatgta ataattcaca ccaattttat taaatgtatt tgcttttca      1800 aaatttaaat tgagctgcta tcaatattaa atgaagttat ggcatccaaa aaaaaaaaa      1860 aaa                                                                    1863
```

<210> SEQ ID NO 6
<211> LENGTH: 1317
<212> TYPE: PRT
<213> ORGANISM: Homo sapiens

<400> SEQUENCE: 6

```
Met Ala Ser Val Lys Val Ala Val Arg Val Arg Pro Met Asn Arg Arg
1               5                   10                  15

Glu Lys Asp Leu Glu Ala Lys Phe Ile Ile Gln Met Glu Lys Ser Lys
            20                  25                  30

Thr Thr Ile Thr Asn Leu Lys Ile Pro Glu Gly Gly Thr Gly Asp Ser
        35                  40                  45

Gly Arg Glu Arg Thr Lys Thr Phe Thr Tyr Asp Phe Ser Phe Tyr Ser
    50                  55                  60
```

```
Ala Asp Thr Lys Ser Pro Asp Tyr Val Ser Gln Glu Met Val Phe Lys
 65                  70                  75                  80

Thr Leu Gly Thr Asp Val Val Lys Ser Ala Phe Glu Gly Tyr Asn Ala
                 85                  90                  95

Cys Val Phe Ala Tyr Gly Gln Thr Gly Ser Gly Lys Ser Tyr Thr Met
            100                 105                 110

Met Gly Asn Ser Gly Asp Ser Gly Leu Ile Pro Arg Ile Cys Glu Gly
        115                 120                 125

Leu Phe Ser Arg Ile Asn Glu Thr Thr Arg Trp Asp Glu Ala Ser Phe
    130                 135                 140

Arg Thr Glu Val Ser Tyr Leu Glu Ile Tyr Asn Glu Arg Val Arg Asp
145                 150                 155                 160

Leu Leu Arg Arg Lys Ser Ser Lys Thr Phe Asn Leu Arg Val Arg Glu
                165                 170                 175

His Pro Lys Glu Gly Pro Tyr Val Glu Asp Leu Ser Lys His Leu Val
            180                 185                 190

Gln Asn Tyr Gly Asp Val Glu Leu Met Asp Ala Gly Asn Ile Asn
        195                 200                 205

Arg Thr Thr Ala Ala Thr Gly Met Asn Asp Val Ser Ser Arg Ser His
210                 215                 220

Ala Ile Phe Thr Ile Lys Phe Thr Gln Ala Lys Phe Asp Ser Glu Met
225                 230                 235                 240

Pro Cys Glu Thr Val Ser Lys Ile His Leu Val Asp Leu Ala Gly Ser
            245                 250                 255

Glu Arg Ala Asp Ala Thr Gly Ala Thr Gly Val Arg Leu Lys Glu Gly
            260                 265                 270

Gly Asn Ile Asn Lys Ser Leu Val Thr Leu Gly Asn Val Ile Ser Ala
        275                 280                 285

Leu Ala Asp Leu Ser Gln Asp Ala Ala Asn Thr Leu Ala Lys Lys Lys
    290                 295                 300

Gln Val Phe Val Pro Tyr Arg Asp Ser Val Leu Thr Trp Leu Leu Lys
305                 310                 315                 320

Asp Ser Leu Gly Gly Asn Ser Lys Thr Ile Met Ile Ala Thr Ile Ser
                325                 330                 335

Pro Ala Asp Val Asn Tyr Gly Glu Thr Leu Ser Thr Leu Arg Tyr Ala
            340                 345                 350

Asn Arg Ala Lys Asn Ile Ile Asn Lys Pro Thr Ile Asn Glu Asp Ala
        355                 360                 365

Asn Val Lys Leu Ile Arg Glu Leu Arg Ala Glu Ile Ala Arg Leu Lys
    370                 375                 380

Thr Leu Leu Ala Gln Gly Asn Gln Ile Ala Leu Leu Asp Ser Pro Thr
385                 390                 395                 400

Ala Leu Ser Met Glu Glu Lys Leu Gln Gln Asn Glu Ala Arg Val Gln
                405                 410                 415

Glu Leu Thr Lys Glu Trp Thr Asn Lys Trp Asn Glu Thr Gln Asn Ile
            420                 425                 430

Leu Lys Glu Gln Thr Leu Ala Leu Arg Lys Glu Gly Ile Gly Val Val
        435                 440                 445

Leu Asp Ser Glu Leu Pro His Leu Ile Gly Ile Asp Asp Leu Leu
    450                 455                 460

Ser Thr Gly Ile Ile Leu Tyr His Leu Lys Glu Gly Gln Thr Tyr Val
465                 470                 475                 480

Gly Arg Asp Asp Ala Ser Thr Glu Gln Asp Ile Val Leu His Gly Leu
                485                 490                 495
```

-continued

```
Asp Leu Glu Ser Glu His Cys Ile Phe Glu Asn Ile Gly Thr Val
            500                 505                 510

Thr Leu Ile Pro Leu Ser Gly Ser Gln Cys Ser Val Asn Gly Val Gln
            515                 520                 525

Ile Val Glu Ala Thr His Leu Asn Gln Gly Ala Val Ile Leu Leu Gly
530                 535                 540

Arg Thr Asn Met Phe Arg Phe Asn His Pro Lys Glu Ala Ala Lys Leu
545                 550                 555                 560

Arg Glu Lys Arg Lys Ser Gly Leu Leu Ser Ser Phe Ser Leu Ser Met
                565                 570                 575

Thr Asp Leu Ser Lys Ser Arg Glu Asn Leu Ser Ala Val Met Leu Tyr
            580                 585                 590

Asn Pro Gly Leu Glu Phe Glu Arg Gln Gln Arg Glu Glu Leu Glu Lys
            595                 600                 605

Leu Glu Ser Lys Arg Lys Leu Ile Glu Glu Met Glu Glu Lys Gln Lys
        610                 615                 620

Ser Asp Lys Ala Glu Leu Glu Arg Met Gln Gln Val Glu Thr Gln
625                 630                 635                 640

Arg Lys Glu Thr Glu Ile Val Gln Leu Gln Ile Arg Lys Gln Glu Glu
                645                 650                 655

Ser Leu Lys Arg Arg Ser Phe His Ile Glu Asn Lys Leu Lys Asp Leu
            660                 665                 670

Leu Ala Glu Lys Glu Lys Phe Glu Glu Arg Leu Arg Glu Gln Gln
            675                 680                 685

Glu Ile Glu Leu Gln Lys Lys Arg Gln Glu Glu Thr Phe Leu Arg
690                 695                 700

Val Gln Glu Glu Leu Gln Arg Leu Lys Glu Leu Asn Asn Asn Glu Lys
705                 710                 715                 720

Ala Glu Lys Phe Gln Ile Phe Gln Glu Leu Asp Gln Leu Gln Lys Glu
                725                 730                 735

Lys Asp Glu Gln Tyr Ala Lys Leu Glu Leu Glu Lys Lys Arg Leu Glu
            740                 745                 750

Glu Gln Glu Lys Glu Gln Val Met Leu Val Ala His Leu Glu Glu Gln
            755                 760                 765

Leu Arg Glu Lys Gln Glu Met Ile Gln Leu Leu Arg Arg Gly Glu Val
        770                 775                 780

Gln Trp Val Glu Glu Lys Arg Asp Leu Glu Gly Ile Arg Glu Ser
785                 790                 795                 800

Leu Leu Arg Val Lys Glu Ala Arg Ala Gly Gly Asp Glu Asp Gly Glu
                805                 810                 815

Glu Leu Glu Lys Ala Gln Leu Arg Phe Phe Glu Phe Lys Arg Arg Gln
            820                 825                 830

Leu Val Lys Leu Val Asn Leu Glu Lys Asp Leu Val Gln Gln Lys Asp
            835                 840                 845

Ile Leu Lys Lys Glu Val Gln Glu Gln Glu Ile Leu Glu Cys Leu
        850                 855                 860

Lys Cys Glu His Asp Lys Glu Ser Arg Leu Leu Lys His Asp Glu
865                 870                 875                 880

Ser Val Thr Asp Val Thr Glu Val Pro Gln Asp Phe Glu Lys Ile Lys
                885                 890                 895

Pro Val Glu Tyr Arg Leu Gln Tyr Lys Glu Arg Gln Leu Gln Tyr Leu
            900                 905                 910

Leu Gln Asn His Leu Pro Thr Leu Leu Glu Glu Lys Gln Arg Ala Phe
```

```
                915                 920                 925
Glu Ile Leu Asp Arg Gly Pro Leu Ser Leu Asp Asn Thr Leu Tyr Gln
    930                 935                 940

Val Glu Lys Glu Met Glu Glu Lys Glu Glu Gln Leu Ala Gln Tyr Gln
945                 950                 955                 960

Ala Asn Ala Asn Gln Leu Gln Lys Leu Gln Ala Thr Phe Glu Phe Thr
                965                 970                 975

Ala Asn Ile Ala Arg Gln Glu Glu Lys Val Arg Lys Lys Glu Lys Glu
                980                 985                 990

Ile Leu Glu Ser Arg Glu Lys Gln Gln Arg Glu Ala Leu Glu Arg Ala
            995                 1000                1005

Leu Ala Arg Leu Glu Arg Arg His Ser Ala Leu Gln Arg His Ser
    1010                1015                1020

Thr Leu Gly Met Glu Ile Glu Glu Gln Arg Gln Lys Leu Ala Ser
    1025                1030                1035

Leu Asn Ser Gly Ser Arg Glu Gln Ser Gly Leu Gln Ala Ser Leu
    1040                1045                1050

Glu Ala Glu Gln Glu Ala Leu Glu Lys Asp Gln Glu Arg Leu Glu
    1055                1060                1065

Tyr Glu Ile Gln Gln Leu Lys Gln Lys Ile Tyr Glu Val Asp Gly
    1070                1075                1080

Val Gln Lys Asp His His Gly Thr Leu Glu Gly Lys Val Ala Ser
    1085                1090                1095

Ser Ser Leu Pro Val Ser Ala Glu Lys Ser His Leu Val Pro Leu
    1100                1105                1110

Met Asp Ala Arg Ile Asn Ala Tyr Ile Glu Glu Val Gln Arg
    1115                1120                1125

Arg Leu Gln Asp Leu His Arg Val Ile Ser Glu Gly Cys Ser Thr
    1130                1135                1140

Ser Ala Asp Thr Met Lys Asp Asn Glu Lys Leu His Asn Gly Thr
    1145                1150                1155

Ile Gln Arg Lys Leu Lys Tyr Glu Arg Met Val Ser Arg Ser Leu
    1160                1165                1170

Gly Ala Asn Pro Asp Asp Leu Lys Asp Pro Ile Lys Ile Ser Ile
    1175                1180                1185

Pro Arg Tyr Val Leu Cys Gly Gln Gly Lys Asp Ala His Phe Glu
    1190                1195                1200

Phe Glu Val Lys Ile Thr Val Leu Asp Glu Thr Trp Thr Val Phe
    1205                1210                1215

Arg Arg Tyr Ser Arg Phe Arg Glu Met His Lys Thr Leu Lys Leu
    1220                1225                1230

Lys Tyr Ala Glu Leu Ala Ala Leu Glu Phe Ala Pro Lys Lys Leu
    1235                1240                1245

Phe Gly Asn Lys Asp Glu Arg Val Ile Ala Glu Arg Arg Ser His
    1250                1255                1260

Leu Glu Lys Tyr Leu Arg Asp Phe Phe Ser Val Met Leu Gln Ser
    1265                1270                1275

Ala Thr Ser Pro Leu His Ile Asn Lys Val Gly Leu Thr Leu Ser
    1280                1285                1290

Lys His Thr Ile Cys Glu Phe Ser Pro Phe Phe Lys Lys Gly Val
    1295                1300                1305

Phe Asp Tyr Ser Ser His Gly Thr Gly
    1310                1315
```